United States Patent
Smoorenburg

(10) Patent No.: US 8,401,656 B2
(45) Date of Patent: *Mar. 19, 2013

(54) PERCEPTION-BASED PARAMETRIC FITTING OF A PROSTHETIC HEARING DEVICE

(75) Inventor: Guido F. Smoorenburg, Soest (NL)

(73) Assignee: Cochlear Limited, Macquarie University, NSW (AU)

( * ) Notice: Subject to any disclaimer, the term of this patent is extended or adjusted under 35 U.S.C. 154(b) by 755 days.

This patent is subject to a terminal disclaimer.

(21) Appl. No.: 12/191,216

(22) Filed: Aug. 13, 2008

(65) Prior Publication Data

US 2009/0043359 A1 Feb. 12, 2009

Related U.S. Application Data

(63) Continuation-in-part of application No. 10/518,812, filed as application No. PCT/AU03/00804 on Jun. 26, 2003.

(30) Foreign Application Priority Data

Jun. 26, 2002 (AU) .......................... PS3182

(51) Int. Cl.
A61N 1/18 (2006.01)
H04R 25/00 (2006.01)
(52) U.S. Cl. .......................... 607/57; 607/55
(58) Field of Classification Search ........... 607/55–57
See application file for complete search history.

(56) References Cited

U.S. PATENT DOCUMENTS

| | | | |
|---|---|---|---|
| 4,114,627 A | 9/1978 | Lewyn et al. | |
| 4,305,396 A | 12/1981 | Wittkampf et al. | |
| 4,343,312 A | 8/1982 | Cals et al. | |
| 4,373,531 A | 2/1983 | Wittkampf et al. | |
| 4,400,590 A * | 8/1983 | Michelson | 607/57 |
| 4,440,590 A | 4/1984 | Collins et al. | |
| 4,532,930 A | 8/1985 | Crosby et al. | |
| 4,543,956 A | 10/1985 | Herscovici | |
| 4,895,152 A | 1/1990 | Callaghan et al. | |
| 4,941,179 A | 7/1990 | Bergenstoff et al. | |
| 5,016,280 A | 5/1991 | Engebretson et al. | |
| 5,034,918 A | 7/1991 | Jeong | |
| 5,172,690 A | 12/1992 | Nappholz et al. | |
| 5,271,397 A | 12/1993 | Seligman et al. | |

(Continued)

FOREIGN PATENT DOCUMENTS

EP 0282336 9/1988
EP 0836363 4/1998

(Continued)

OTHER PUBLICATIONS

Abbas et al., "Electrically Evoked Compound Action Potentials Recorded from Subjects Who Use the Nucleus CI24M Device," Ann. Otol. Rhino!. Laryngol. Suppl.; Dec. 2000; 185: pp. 6-9.

(Continued)

*Primary Examiner* — Rex R Holmes
(74) *Attorney, Agent, or Firm* — Kilpatrick, Townsend & Stockton, LLP.

(57) ABSTRACT

According to one aspect of the present invention, there is provided a method of adjusting an established initial operational settings profile, the profile having two or more operational setting values for a speech processor of a recipient's cochlear implant, comprising: setting one or more profile adjustment functions with one or more function parameters; and modifying concurrently said two or more operational setting values in said operational settings profile using each of said set profile adjustment functions.

21 Claims, 9 Drawing Sheets

U.S. PATENT DOCUMENTS

| | | | |
|---|---|---|---|
| 5,277,694 A | 1/1994 | Leysieffer et al. | |
| 5,278,994 A | 1/1994 | Black et al. | |
| 5,565,503 A | 10/1996 | Garcia et al. | |
| 5,626,629 A * | 5/1997 | Faltys et al. | 607/57 |
| 5,674,264 A | 10/1997 | Carter et al. | |
| 5,748,651 A | 5/1998 | Sheynblat | |
| 5,758,651 A | 6/1998 | Nygard et al. | |
| 5,895,416 A | 4/1999 | Barreras, Sr. et al. | |
| 5,963,904 A | 10/1999 | Lee et al. | |
| 6,002,966 A | 12/1999 | Loeb et al. | |
| 6,157,861 A | 12/2000 | Faltys et al. | |
| 6,205,360 B1 | 3/2001 | Carter et al. | |
| 6,289,247 B1 * | 9/2001 | Faltys et al. | 607/57 |
| 6,428,484 B1 | 8/2002 | Battmer et al. | |
| 6,430,402 B1 | 8/2002 | Agahi-Kesheh | |
| 6,463,328 B1 | 10/2002 | John | |
| 6,537,200 B2 | 3/2003 | Leysieffer et al. | |
| 6,565,503 B2 | 5/2003 | Leysieffer et al. | |
| 6,575,894 B2 | 6/2003 | Leysieffer et al. | |
| 6,600,955 B1 | 7/2003 | Zierhofer | |
| 6,697,674 B2 | 2/2004 | Leysieffer | |
| 6,731,767 B1 | 5/2004 | Blamey et al. | |
| 6,751,505 B1 | 6/2004 | Van Den Honert et al. | |
| 6,915,166 B1 | 7/2005 | Stecker et al. | |
| 7,043,303 B1 | 5/2006 | Overstreet | |
| 7,076,308 B1 | 7/2006 | Overstreet et al. | |
| 7,082,332 B2 | 7/2006 | Blamey et al. | |
| 7,117,038 B1 | 10/2006 | Overstreet | |
| 7,711,133 B2 | 5/2010 | Goorevich et al. | |
| 2001/0049466 A1 | 12/2001 | Leysieffer et al. | |
| 2002/0026091 A1 | 2/2002 | Leysieffer | |
| 2004/0098063 A1 | 5/2004 | Goetz | |
| 2004/0167586 A1 | 8/2004 | Overstreet | |
| 2005/0015133 A1 | 1/2005 | Ibrahim et al. | |
| 2005/0101878 A1 | 5/2005 | Daly et al. | |
| 2005/0107845 A1 | 5/2005 | Wakefield et al. | |
| 2005/0245991 A1 | 11/2005 | Faltys et al. | |
| 2006/0235332 A1 | 10/2006 | Smoorenburg | |
| 2007/0084995 A1 | 4/2007 | Newton et al. | |
| 2007/0255344 A1 | 11/2007 | Van Dijk | |
| 2008/0319508 A1 | 12/2008 | Botros et al. | |
| 2010/0268302 A1 | 10/2010 | Botros | |

FOREIGN PATENT DOCUMENTS

| | | |
|---|---|---|
| EP | 2 222 369 A1 | 9/2010 |
| WO | 9210134 | 6/1992 |
| WO | 9324176 | 12/1993 |
| WO | 9414376 | 7/1994 |
| WO | 9501709 | 1/1995 |
| WO | 9612383 | 4/1996 |
| WO | 9709863 | 3/1997 |
| WO | 9748447 | 12/1997 |
| WO | 00/52963 A1 | 9/2000 |
| WO | WO 00/52963 | 9/2000 |
| WO | 0076436 | 12/2000 |
| WO | 0113991 | 3/2001 |
| WO | 01/56521 A1 | 8/2001 |
| WO | 02/082982 A1 | 10/2002 |
| WO | 03070322 | 8/2003 |
| WO | 2004/004412 A1 | 1/2004 |
| WO | 2004/021885 | 3/2004 |
| WO | 2004/080532 A1 | 9/2004 |
| WO | 2005/006808 A1 | 1/2005 |
| WO | 20051122887 | 12/2005 |
| WO | WO 2008/031169 A1 | 3/2008 |
| WO | WO 2009/076721 A1 | 6/2009 |
| WO | 20091124035 | 10/2009 |

OTHER PUBLICATIONS

Abbas et al., "Summary of Results Using the Nucleus CI24M Implant to Record the Electrically Evoked Compound Action Potential," Ear and Hearing, vol. 20(1), Feb. 1999, pp. 45-59.

Australian Examiner's First Report for Patent Application No. 2005254100, dated Dec. 17, 2009.

Baumgarte et al., "A Nonlinear Psychoacoustic Model Applied to the ISO MPEG Layer 3 Coder," Proc. 99th Conv. Aud. Eng. Soc., New York, NY, Oct. 1995, preprint 4087.

Brown et al., "Electrically Evoked Whole-Nerve Action Potentials: Data from Human Cochlear Implant Users," Journal of Acoustical Society of America, vol. 18, No. 3, Sep. 1990, pp. 1385-1391.

Charasse et al., Automatic Analysis of Auditory Nerve Electrically Evoked Compound Action Potential with an Artificial Neural Network, Artificial Intelligence in Medicine, Mar. 3, 2004, pp. 221-229.

Charasse et al., "Comparison of Two Different Methods to Automatically Classify Auditory Nerve Responses Recorded with NRT System," Acta Acustica United with Acustica, vol. 90, Jan. 22, 2004, pp. 512-519.

Cohen et al., "Spatial Spread of Neural Excitation in Cochlear Implant Recipients: Comparison of Improved ECAP Method and Psychophysical Forward Masking," Hearing Research, 179 (2003), pp. 72-87.

Cohen et al., "Spatial Spread of Neural Excitation: Comparison of Compound Action Potential and Forward-Masking Data in Cochlear Implant Recipients," International Journal of Audiology 2004, 43, pp. 346-355.

Delgado et al., "Automated Auditory Brainstem Response Interpretation," IEEE Engineering in Medicine and Biology, Apr./May 1994, pp. 227-237.

Dijk et al., "Development of a Prototype Fully-Automated Intra-Operative ECAP Recording Tool, Using NRT(TM) v3," 2003 Conference on Implantable Auditory Prostheses, 2003, 7 pages total.

Dillier et al., "Measurement of the Electrically Evoked Compound Action Potential via a Neural Response Telemetry System," Annals of Otology, Rhinology & Laryngology, vol. 111, No. 5, May 2002, pp. 407-414.

Edler et al., "ASAC-Analysis/Synthesis Audio Codec for Very Low Bit Rates," Proc. 100th Cony. Aud. Eng. Soc., May 1996, preprint 4179.

European Search Report (Annex) for EP 01 95 9971, dated Aug. 2, 2005.

Franck et al., "Estimation of Psychophysical Levels Using the Electrically Evoked Compound Action Potential Measured with the Neural Response Telemetry Capabilities of Cochlear Corporation's CI24M Device," Ear & Hearing, vol. 22, No. 4, Aug. 2001, pp. 289-299.

Franck, "A Model of a Nucleus 24 Cochlear Implant Fitting Protocol Based on the Electrically Evoked Whole Nerve Action Potential," Ear & Hearing, vol. 23, No. 1S, Feb. 2002, pp. 67S-71S.

Hartmann et al., "Evoked Potentials from the Auditory Nerve Following Sinusoidal Electrical Stimulation of the Cochlea: New Possibilities for Preoperative Testing in Cochlear-Implant Candidates?" Acta Otoloaryngol (Stockh) 1994,114, pp. 495-500.

Hughes et al., "Comparison of EAP Thresholds with MAP Levels in the Nucleus 24 Cochlear Implant: Data from Children," Ear and Hearing, vol. 21(2), Apr. 2000, pp. 164-174.

International Preliminary Examination Report for PCT/FR2003/000577, dated May 7, 2004 (English translation).

International Preliminary Examination Report for PCT/AU01/01032, dated Apr. 10, 2002.

International Preliminary Examination Report for PCT/AU02/00500, dated Feb. 12, 2003.

International Preliminary Report on Patentability for PCT/US20051021207, dated Dec. 20, 2006.

International Search Report for PCT/FR2003/00577, dated Jul. 4, 2003 (English translation).

International Search Report for PCT/US2005/21207, dated Feb. 8, 2006.

International Search Report for PCT/US2009/038932, dated Jun. 5, 2009.

International Search Report for PCT/AU01/01032, dated Oct. 5, 2001.

International Search Report for PCT/AU02/00500, dated Jun. 26, 2002.

Lai et al., "A Simple Two-Component Model of the Electrically Evoked Compound Action Potential in the Human Cochlea," Audiology & Neuro—Otology, Nov./Dec. 2000; 5: pp. 333-345.

Miller et al., "An Improved Method of Reducing Stimulus Artifact in the Electrically Evoked Whole-Nerve Potential," Ear & Hearing, vol. 21, No. 4, Aug. 2000, pp. 280-290.

Nicolai et al., Performance of Automatic Recognition Algorithms in Nucleus Neural Response Telemetry (NRT(TM)), 2003 Conference on Implantable Auditory Prostheses, 2003, one page total.

Riedmiller et al., "A Direct Adaptive Method for Faster Backpropagation Learning: The RPROP Algorithm," Proceedings of the International IEEE Conference on Neural Networks—1993, vol. 1, Mar. 28-Apr. 1, 1993, pp. 586-591.

Seyle et al., "Speech Perception Using Maps Based on Neural Response Telemetry Measures," Ear & Hearing, vol. 23, No. 1S, Feb. 2002, pp. 72S-79S.

Smoorenburg et al., "Speech Perception in Nucleus CI24M Cochlear Implant Users with Processor Settings Based on Electrically Evoked Compound Action Potential Thresholds," Audiology & Neuro—Otology, Nov./Dec. 2002; 7: pp. 335-347.

Supplementary Partial European Search Report for EP 02 71 7863 dated, Oct. 18, 2005.

Thai-Van et al., "Modeling the Relationship Between Psychophysical Perception and Electrically Evoked Compound Action Potential Threshold in Young Cochlear Implant Recipients: Clinical Implications for Implant Fitting," Cinical Neurophysiology 115 (2004), pp. 2811-2824.

Vannier et al., "Objective Detection of Brainstem Auditory Evoked Potentials with a Priori Information from Higher Presentation Levels," Artificial Intelligence in Medicine, Feb. 21, 2002, pp. 283-301.

Written Opinion for PCT/US2009/038932, dated Jun. 5, 2009.

Written Opinion for PCT/US20051021207, dated Feb. 8, 2006.

Austrian First Office Action (English Translation) for Austrian Official file No. 3B A 9165/2003-1, related to PCT/AU2003/000804, dated Mar. 20, 2007.

PCT/AU2003/000804 Austrian First Office Action (English Translation).

Brown et al. "The Relationship Between EAP and EABR Thresholds and Levels Used to Program the Nucleus 24 Speech Processor: Data from Adults" Ear and Hearing. 2000, Lippincott Williams & Wilkins, U.S.A.

PCT/AU2003/000804 International Preliminary Examination Report. Completed Oct. 12, 2004.

PCT/AU2003/000804 Written Opinion. Mailed Oct. 16, 2003.

PCT/AU2003/000804 International Search Report. Mailed Aug. 26, 2003.

European Application No. 05762889.3, Supplemental European Search Report mailed on May 11, 2010, 3 Pages.

International Application No. PCT/AU2008/001865, International Preliminary Report on Patentability mailed on Jun. 22, 2010, 5 Pages.

International Application No. PCT/AU2008/001865, International Search Report and Written Opinion mailed on Mar. 12, 2009, 7 Pages.

International Application No. PCT/US2009/038932, International Preliminary Report on Patentability mailed on Jun. 21, 2010, 9 Pages.

* cited by examiner

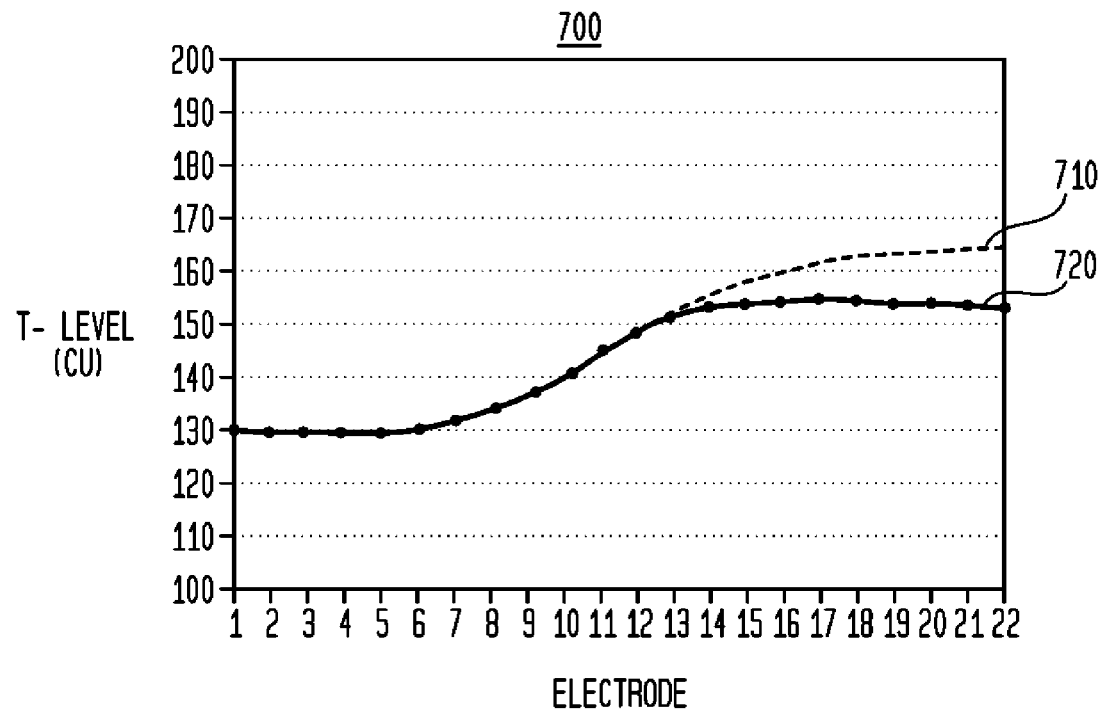

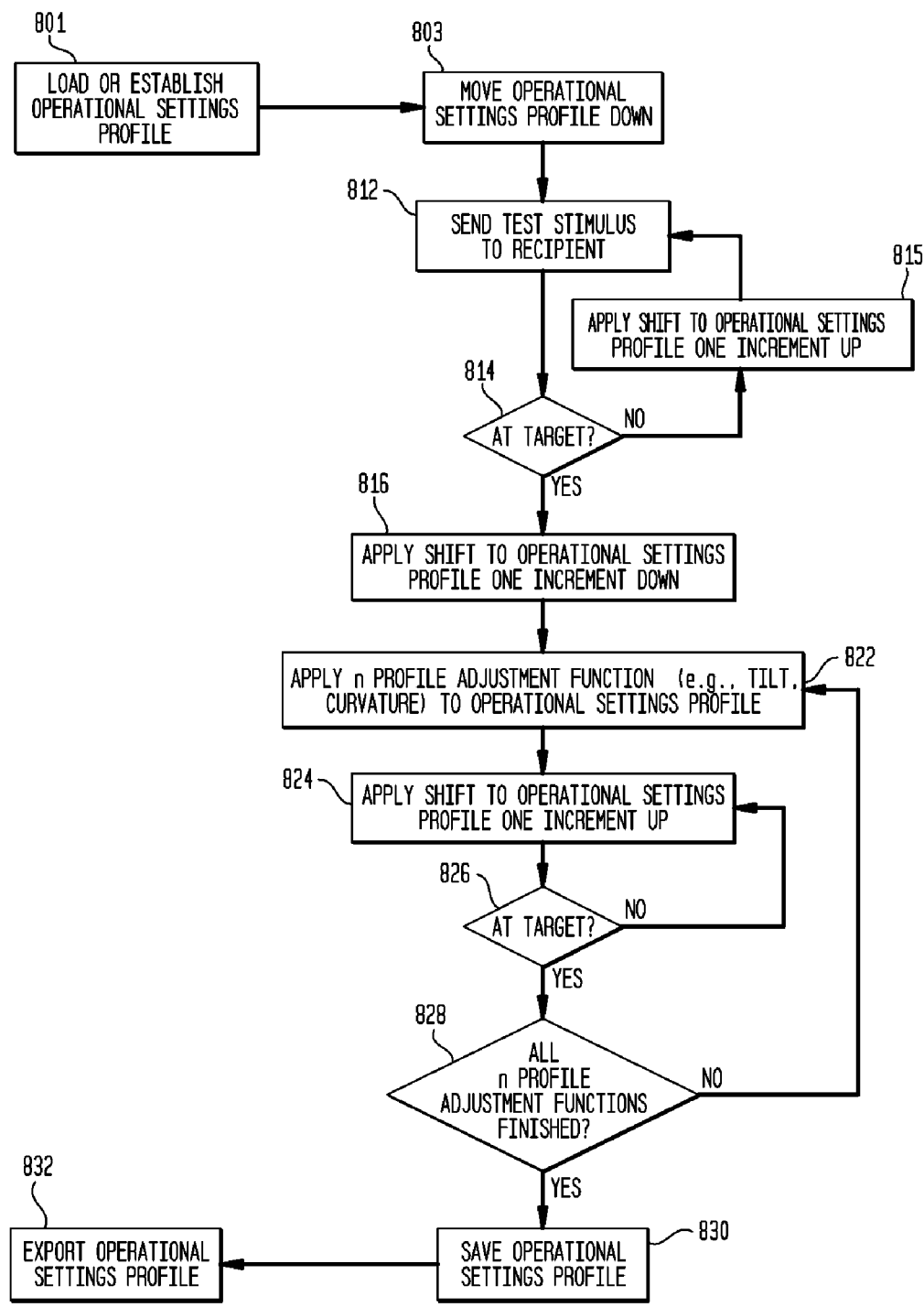

PERCEPTION-BASED PARAMETRIC FITTING OF A PROSTHETIC HEARING DEVICE

CROSS-REFERENCE TO RELATED APPLICATIONS

This application is a Continuation-In-Part Application of application Ser. No. 10/518,812, filed Oct. 11, 2005, which is a National Phase Application of International Application No. PCT/AU03/00804, filed on Jun. 26, 2003, which claims priority from Australian Patent Application No. PS 3182, filed Jun. 26, 2002. The above applications are hereby incorporated by reference herein.

BACKGROUND

1. Field of the Invention

The present invention relates generally to clinically fitting a prosthetic hearing device to a recipient, and more specifically, to perception-based parametric fitting of a prosthetic hearing device.

2. Related Art

Prosthetic hearing devices, such as hearing aids, middle-ear implants, Cochlear™ implants, auditory brain stimulators and other such devices have been developed to assist people who were born with or developed hearing impairments. For example, cochlear implants are designed to assist individuals who are profoundly deaf or severely hearing impaired, by enabling them to experience hearing sensation representative of the natural hearing sensation. (Cochlear™ implants are commonly referred as Cochlear™ prostheses, Cochlear™ devices, etc.; simply "cochlear implants" herein.) In most such cases, these individuals have an absence of or destruction of the hair cells in the cochlea that naturally transduce acoustic signals into nerve impulses which are interpreted by the brain as sound. The cochlear implant bypasses the hair cells by directly delivering to the auditory nerves electrical stimulation representative of the sound.

Cochlear implants have traditionally consisted of two parts, an external sound processor unit and an implanted receiver/stimulator unit. Typically worn on the body of the recipient, the external sound processor unit primarily detects external sound using an audio pickup device such as a microphone, and by processing the received sound using an appropriate speech processing strategy, converts the detected sound into a coded signal.

This coded signal is then sent to the receiver/stimulator unit which is implanted in, for example, the mastoid bone of the recipient, via a transcutaneous link. The receiver/stimulator unit then processes this coded signal to generate a series of stimulation sequences which are then applied directly to the auditory nerve via a series of electrodes positioned within the cochlea.

With improvements in technology the external sound processor and implanted stimulator unit may be combined to produce a totally implantable cochlear implant unit capable of operating without an external device. In such a device, a microphone or other audio pickup device would be implanted within the body of the recipient, for example in the ear canal or within the stimulator unit. Detected sound is directly processed by a speech processor within the stimulator unit, with the subsequent stimulation signals delivered without the need for any transcutaneous transmission of signals. Such a device would, however, still have the capability to communicate with an external device when necessary, particularly for program upgrades and/or implant interrogation, and if the operating configuration of the device required alteration.

Typically, following surgical implantation of a cochlear implant, the recipient must have the implant fitted or customized to conform to the specific physiology and needs of that recipient. This procedure, often referred to as programming or "mapping," results in the creation of a collection of data commonly referred to as a "program" or "map." A map contains a set of instructions for the sound processor, including the stimulation mode and sound processing strategy(ies) chosen for the recipient. The map also includes operational setting values such as a value corresponding to the lowest amplitude at which the recipient hears a sound, referred to as the threshold level, or T-level, and the maximum amplitude at which the recipient comfortably hears the sound, referred to as the comfort level, or C-level. The map is utilized by the sound processor to ensure stimulation from the implant provides the recipient with comfortable and useful auditory perception.

A fundamental aspect of programming a cochlear implant is the collection and determination of recipient-specific operational setting values such as the noted T- and C-levels. Such operational setting values vary for each stimulation channel and recipient. Measuring such recipient-specific settings requires an experienced clinician or audiologist to first present a stimulus to each stimulation channel of the recipient's cochlear implant, and then to measure or receive a resulting response.

Given that obtaining measurements for each stimulation channel is time consuming, and given that the measurement process is repeated over potentially a large number of channels, conventional programming techniques are a laborious task requiring the clinician to have much experience and expertise, while also requiring the recipient to provide adequate feedback. This is further compounded by the fact that the recipient's perception of a provided stimulus may change subsequent to the initial implantation and map creation. In some cases, the recipient's perception of a provided stimulus may stabilize months after implantation.

SUMMARY

According to one aspect of the present invention, there is provided a method of adjusting an established initial operational settings profile, the profile having two or more operational setting values for a speech processor of a recipient's cochlear implant, comprising: setting one or more profile adjustment functions with one or more function parameters; and modifying concurrently said two or more operational setting values in said operational settings profile using each of said set profile adjustment functions.

According to another aspect of the present invention, there is provided a programmable apparatus configured to adjust an established initial operational settings profile, the profile having two or more operational setting values for a speech processor of a recipient's cochlear implant, comprising: a processor configured to execute computer code; a software package executed by said processor and configured to receive one or more operator inputs; an interface configured to communicatively couple said processor with the auditory stimulation system and further configured to retrieve and store the operational settings profile, wherein said software package is configured to set one or more profile adjustment functions with one or more function parameters, and further configured to modify concurrently said two or more operational setting values in said operational settings profile using each of said set profile adjustment functions.

According to yet another aspect of the present invention, there is provided a programmable apparatus configured to adjust an established initial operational settings profile, the profile having two or more operational setting values for a speech processor of a recipient's cochlear implant, comprising: means for setting one or more profile adjustment functions with one or more function parameters; and means for modifying concurrently said two or more operational setting values in said operational settings profile.

BRIEF DESCRIPTION OF THE DRAWINGS

Embodiments of the invention will now be described, by way of example only, with reference to the accompanying drawings, in which:

FIG. 7 is a graphical depiction of the operational settings profile of FIG. 4 after having a tilt profile adjustment function with a parameter of 25 CU applied, as depicted in FIG. 6, followed by a curvature profile adjustment function with a function parameter being applied to the operational settings profile depicted in FIG. 6 according to an embodiment of the present invention; and FIG. 8A-8C are flowcharts of the process of adjusting operational settings profiles according to an embodiment of the present invention.

DETAILED DESCRIPTION

Aspects of the present invention are generally directed to fitting a prosthetic hearing device by modifying previously-established operational setting values of a sound processor. Many operational setting values of a sound processor have a value that varies across the plurality of stimulation channels of the implant. The collection of operational setting values across the stimulation channels is commonly referred to as an operational settings profile. A profile adjustment function is implemented by a clinician, audiologist, or another ("operator" herein) that concurrently adjusts a plurality of operational setting values; that is, at least a portion of the operational settings profile. The profile adjustment function, which may be one of a plurality of such functions available to the operator, modifies the previously-established values of the operational setting. Although such modification of operational setting values may be performed at any time, it should be appreciated that the programming of prosthetic hearing devices is typically repeated at least once subsequent to device implantation and after the device has stabilized. In contrast to conventional approaches in which operational setting values are individually determined and adjusted, implementing a profile adjustment function in accordance with the teachings of the present invention results in the modification of the setting values in substantially less time and with less effort.

Aspects and embodiments of the present invention may be implemented in connection with a prosthetic hearing device such as a hearing aid, middle ear implant, or cochlear implant or other such device now or later developed. An example of such a prosthetic hearing device is the cochlear implant illustrated in FIG. 1. Specifically, FIG. 1 is a perspective view of an exemplary cochlear implant 100 which may be fitted using embodiments of the programming techniques of the present invention.

Cochlear implants use direct electrical stimulation of auditory nerve cells to bypass absent or defective hair cells that normally transduce acoustic vibrations into neural activity. Such devices generally use an electrode array inserted into the scala tympani of the cochlea so that the electrodes may differentially activate auditory neurons that normally encode differential pitches of sound. Auditory brain stimulators are used to treat a smaller number of recipients with bilateral degeneration of the auditory nerve. For such recipients, the auditory brain stimulator provides stimulation of the cochlear nucleus in the brainstem, typically with a planar electrode array; that is, an electrode array in which the electrode contacts are disposed on a two dimensional surface that can be positioned proximal to the brainstem.

Figure 1:
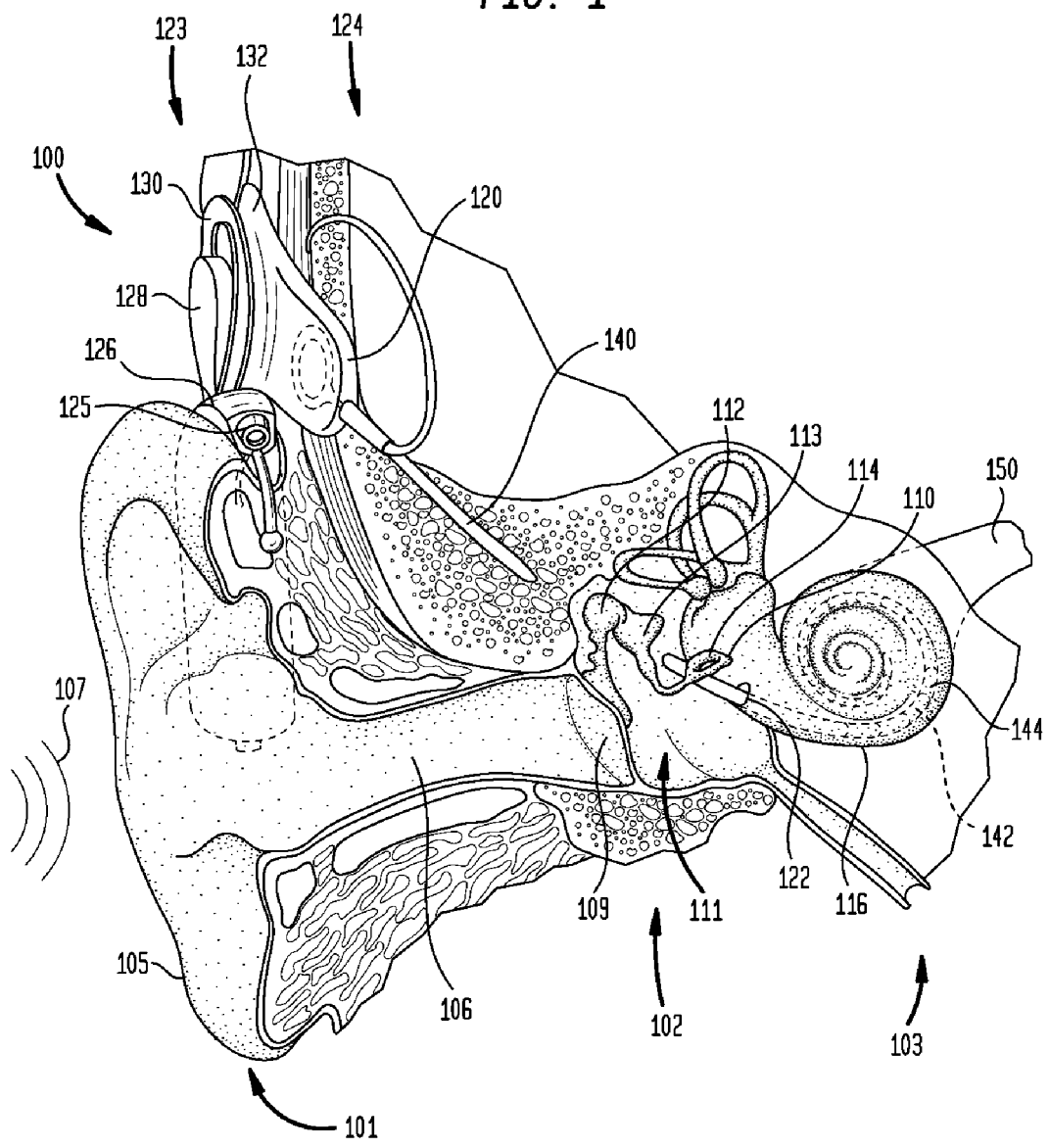
FIG. 1 is an exemplary hearing prosthesis which may be advantageously implemented with embodiments of the present invention.

FIG. 1 depicts a cut-away view of the relevant components of outer ear 101, middle ear 102 and inner ear 103, which are described next below. In a fully functional ear, outer ear 101 comprises an auricle 105 and an ear canal 106. An acoustic pressure or sound wave 107 is collected by auricle 105 and channeled into and through ear canal 106. Disposed across the distal end of ear cannel 106 is a tympanic membrane 109 which vibrates in response to acoustic wave 107. This vibration is coupled to oval window or fenestra ovalis 110 through three bones of middle ear 102, collectively referred to as the ossicles 111 and comprising the malleus 112, the incus 113 and the stapes 114. Bones 112, 113 and 114 of middle ear 102 serve to transform the acoustic wave into a mechanical vibration, causing oval window 110 (together with tympanic membrane) to articulate, or vibrate. Such vibration sets up waves of fluid motion within cochlea 116. Such fluid motion, in turn, activates tiny hair cells (not shown) that line the inside of cochlea 116. Activation of the hair cells causes appropriate nerve impulses to be transferred through the spiral ganglion cells (not shown) and auditory nerve 150 to the brain (also not shown), where they are perceived as sound. In deaf persons, there is an absence or destruction of the hair cells. Cochlear implant 100 is needed to directly stimulate the spiral ganglion cells to provide a hearing sensation to the recipient.

FIG. 1 also shows how a cochlear implant 100 is positioned in relation to outer ear 101, middle ear 102 and inner ear 103. Cochlear implant 100 comprises external component assembly 123 which is directly or indirectly attached to the body of the recipient, and an internal component assembly 124 which is temporarily or permanently implanted in the recipient. External assembly 123 comprises microphone 125 for detecting sound which is outputted to a BTE (Behind-The-Ear) speech processing unit 126 that generates coded signals and are provided to an external transmitter unit 128, along with power from a power source such as a battery (not shown). External transmitter unit 128 comprises an external coil 130 and, preferably, a magnet (also not shown) secured directly or indirectly in external coil 130. Internal components 124 comprise an internal receiver unit 132 having an internal coil (not shown) that receives and transmits power and coded signals from external assembly 123 to a stimulator unit 120 to apply the coded signal along an electrode assembly 140. Electrode assembly 140 enters cochlea 116 at cochleostomy region 122 and has one or more electrodes 142 is positioned to be substantially aligned with portions of cochlea 116.

Cochlea 116 is tonotopically mapped with each region of the cochlea being responsive to acoustic and/or stimulus signals in a particular frequency range. To accommodate this property of cochlea 116, cochlear implant 100 includes an array 144 of electrodes 142 each constructed and arranged to deliver appropriate stimulating signals to particular regions of cochlea 116, each representing a different frequency component of a received audio signal. Signals generated by stimulator unit 120 are applied by electrodes 142 of electrode array 144 to cochlea 116, thereby stimulating the auditory neuron 116. It should be appreciated that although in the embodiment shown in FIG. 1 electrodes 142 are arranged in an array 144, other arrangements are possible.

In one example, electrode array 144 may include a plurality of independent electrodes 142 each of which may be independently stimulated. For example, in one embodiment employing Cochlear's Nucleus 24 system, electrode array 144 includes 22 independent electrodes each of which stimulates an area of the auditory nerve 150 of the recipient's cochlea 116. As one of ordinary skill in the art is aware, low-frequency sounds stimulate the basilar membrane most significantly at its apex, while higher frequencies more strongly stimulate the basilar membrane's base. Thus, electrodes 142 of electrode array 144 located near the base of the cochlea are used to simulate high frequency sounds while electrodes closer to the apex are used to simulate lower frequency sounds. Typically, in such a system, speech processing unit 126 stimulates only the electrodes with the largest signals. For example, cochlear implant 100 may estimate the outputs for each of the 22 electrodes 142 and select the ones with the largest amplitude (that is, maxima). The number of maxima selected may vary, for example, between five (5) and ten (10), depending on a variety of factors. Moreover, the rate of stimulation, often referred to in units of pulses per second, may also vary. Each of the applied maxima will be referred to herein as a channel of stimulation (or stimulation channel). Thus, in an example in which eight (8) maxima are applied, the system will be described as applying eight (8) channels of stimulation.

As one of ordinary skill in the art will appreciate, embodiments of the present invention may be used in combination with any speech strategy now or later developed including, but not limited to, Continuous Interleaved Sampling (CIS), Spectral PEAK Extraction (SPEAK), and Advanced Combination Encoders (ACE™). An example of such speech strategies is described in U.S. Pat. No. 5,271,397, the entire contents and disclosures of which is hereby incorporated by reference herein. Other examples also may also include front-end processing algorithms such as those described in U.S. Pat. No. 6,731,767 entitled 'Adaptive dynamic range of optimization sound processor,' WO 2005/006808 entitled 'Method and Device for Noise Reduction'. Moreover, a genetic algorithm may be used to optimize the map for features such as, but not limited to: rate, growth function and the like, as described in WO 2004/080532 entitled 'Cochlear implant System with Map Optimization Using a Genetic Algorithm. The above references are hereby incorporated by reference herein in their entireties. The present invention may also be used with other speech coding strategies now or later developed. Certain embodiments of the present invention may be used on Cochlear Limited's Nucleus™ implant system that uses a range of coding strategies alternatives, including SPEAK, ACE™, and CIS.

Figure 2:
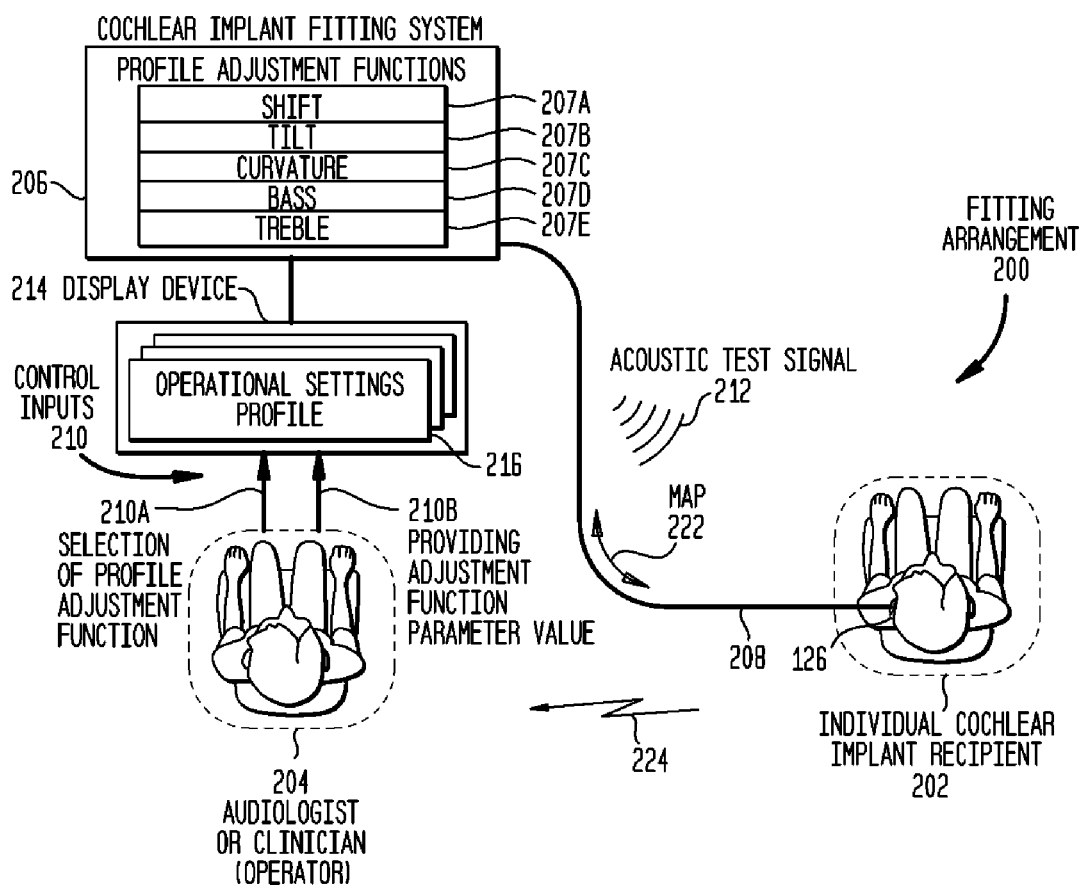
FIG. 2 is a schematic diagram illustrating one exemplary cochlear implant fitting system in which one embodiment of a prosthetic hearing device fitting system configured in accordance with the teachings of the present invention is implemented to fit a cochlear implant to a recipient.

FIG. 2 is a schematic diagram illustrating one exemplary cochlear implant fitting system in which embodiments of a prosthetic hearing device fitting system configured in accordance with the teachings of the present invention is implemented to fit a cochlear implant to a recipient.

As one of ordinary skill in the art would appreciate, the characteristics and code transmitted by cochlear implant 100 are dependent in part on the effectiveness with which the implant is fit to a cochlear implant 100 of an individual recipient 202. Fitting of cochlear implant 100 (also commonly referred to as "adjusting" or "programming" or "mapping") creates a set of instructions (data or code; "mapping data" 222 herein) that defines the specific characteristics used to stimulate electrodes 142 of the implanted electrode array. This set of instructions is commonly referred to as the recipient's "program" or "map."

As shown in FIG. 2, an operator such as an audiologist or clinician 204 uses a hearing implant fitting system 206 ("fitting system" herein) comprising interactive software and computer hardware to create individualized recipient map data 222 which is digitally stored on system 206 and ultimately downloaded to the memory of speech processor 126 of recipient 202. System 206 is programmed and/or implements software programmed to carry out one or more of the functions of mapping, neural response measuring, acoustic stimulating, and recording of neural response measurements and other stimuli. Such features and operations are generally well-known to those of ordinary skill in the art and, therefore, are not described further herein.

Today, most cochlear implants require at least two values to be set for each stimulating electrode 142. These values are referred to as the Threshold level (commonly referred to as the "THR" or "T-level;" "threshold level") and the Maximum Comfortable Loudness level (commonly referred to as the Most Comfortable Loudness level, "MCL," "M-level," or "C;" simply "comfort level"). Threshold levels are comparable to acoustic threshold levels; comfort levels indicate the level at which a sound is loud but comfortable. It should be appreciated that although the terminology and abbreviations are device-specific, the general purpose of threshold and comfort levels is common across many commercially-available cochlear implants: to determine a recipient's electrical dynamic range.

Because of the currently common usage of threshold and current levels, exemplary embodiments of the present invention are described herein in the context of determining such values for cochlear implant 100. As one of ordinary skill in the art would appreciate, however, the perception-based parametric fitting of the present invention may be used to modify previously-established values of other operational setting values in cochlear implants or other prosthetic hearing device now or later developed.

Advances in cochlear implant technology have resulted in a relatively complex fitting process. Today's cochlear implants offer a number of sophisticated operational setting values that can be manipulated to improve sound quality and speech understanding. As noted, embodiments of the present invention are generally directed to perception-based parametric fitting of cochlear implant 100. As will be described in detail below, embodiments of the present invention allow for the operational settings profiles to be manipulated by preprogrammed profile adjustment functions.

Aspects of the present invention are generally directed to fitting a prosthetic hearing device such as a cochlear implant by modifying previously-established operational setting values of a sound processor. As noted, many operational setting values of a sound processor have a value that varies across the plurality of stimulation channels of the implant. The collection of values for each operational setting across the stimulation channels is commonly referred to as a profile.

As shown in FIG. 2, multiple pre-programmed profile adjustment functions 207A-207E are available from which the operator may select. It is to be understood that adjustment functions 207A-207E (collectively referred to as "adjustment functions 207") as shown in FIG. 2 represent only exemplary adjustment functions which may be used in conjunction with the present invention and are not intended to represent all possible adjustment functions possible.

For each selected profile adjustment function 207, operator 204 provides 210B parameter values for the selected adjustment function 207. The parameter values may be provided using a graphical user interface (GUI) in conjunction with an input device such as a keyboard, mouse, light pen, touchscreen, mechanical dial, among others.

Upon control inputs 210 provided by operator 204 to first select a pre-programmed function 207 and then providing parameter values 210B for the selected adjustment function 207 as described above, cochlear implant fitting system 206 will, in one embodiment of the present invention, automatically begin applying the selected adjustment function with the received parameter values to modify the operational settings profile. In other embodiments of the present invention, cochlear implant fitting system 206 will begin applying the selected adjustment function upon receiving another control input 210 from operator 204 indicating commencement of the operation such as a "RUN", "EXECUTE" or "GO" or other such command (not shown). In certain embodiments of the present invention, the selected profile adjustment function will modify only a subset of the values contained in the applicable profile. In other embodiments of the present invention, the selected profile adjustment function will modify the entire profile. In yet further embodiments of the present invention, selecting a particular profile adjustment function 207 will actually execute two or more profile adjustment functions 207 in order to achieve the selected function 207. For example, where the selected profile adjustment function is the "BASS" function 207D, cochlear implant fitting system 206 will modify the operational settings profile by first applying the tilt function followed by the curvature function, as will be described further below in conjunction with FIGS. 6 and 7.

Operational settings profiles 216 are displayed on a display device 214, although any apparatus for presenting such data may be utilized. By enabling the audiologist or clinician to operate fitting arrangement 200 by selecting a profile adjustment function 210A and then entering in a few function parameters 210B, which are then used to modify more than just a single sound processor setting, the operational settings profile for a recipient may be modified much more efficiently.

Figure 3:
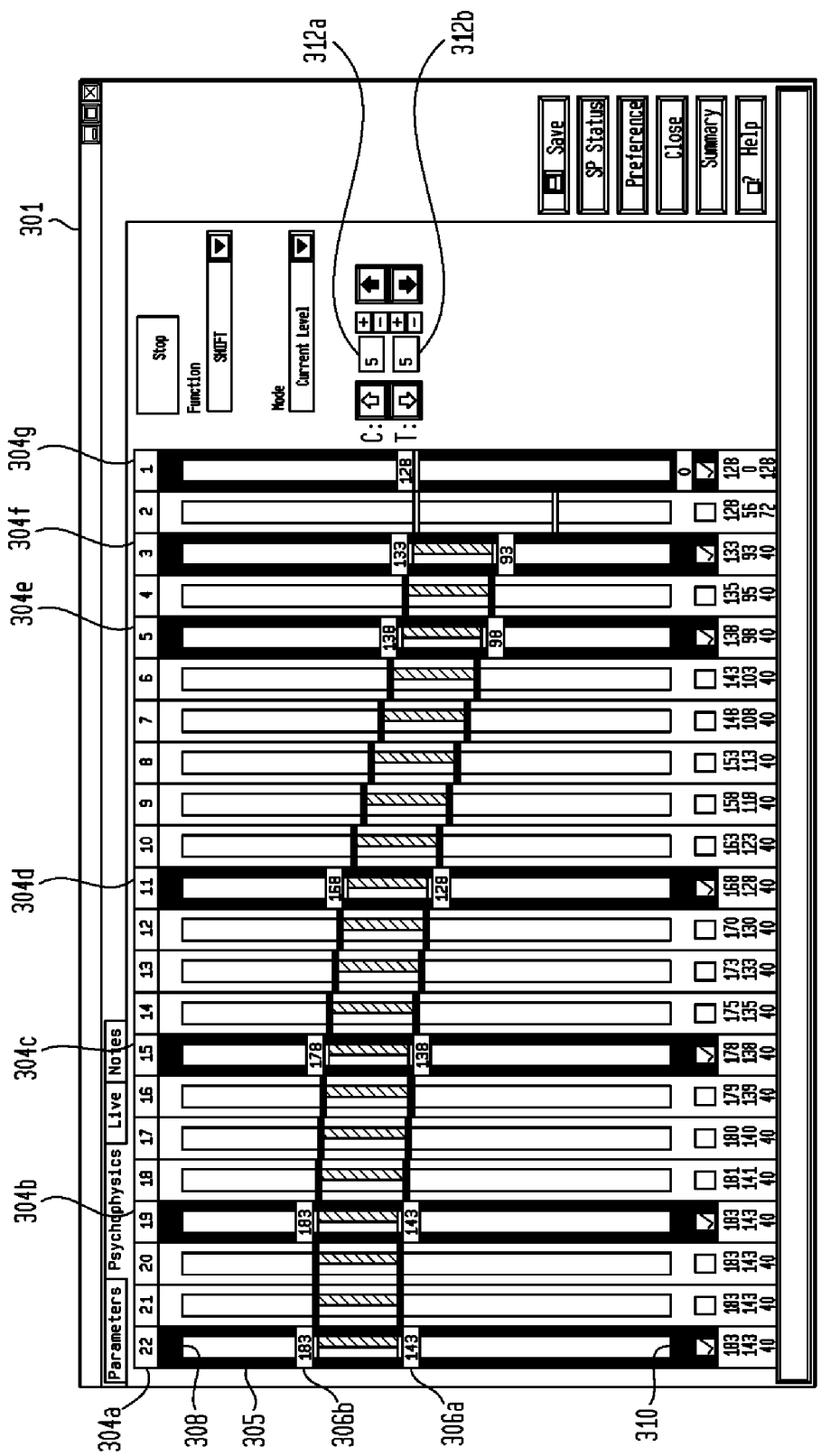
FIG. 3 is a graphical user interface presented on the display of a fitting system in accordance with one embodiment of the present invention.

An exemplary GUI 301 is shown in FIG. 3. The operator's 804 GUI 301 the operator with a user interface that allows the operator to enter function parameters or values for a given profile adjustment function which will be used by the function to modify the operational settings profile. Such function parameters are entered by the audiologist using value entry fields 312A and 312B, or through the use of physical or virtual sliders, physical or virtual dials, buttons or other data entry devices (not shown).

Threshold (T) levels 306A may be obtained using an ascending presentation, followed by a standard bracketing procedure. Comfort (C) levels may be obtained through a method referred to as loudness scaling. This occurs while recipient 202 reports on the level of loudness and comfort. In adult cochlear implant recipients, threshold and comfort levels are typically measured using verbal feedback from recipient 202. For children, who often lack the listening experience, language, or conceptual development to perform specific fitting tasks, audiologists and clinicians must often rely on clinical intuition and trial and error to appropriately estimate comfort levels for young recipients. The above and other feedback is generally referred to by reference numeral 224 in FIG. 2.

Note that although cochlear implant 100 has been described as comprising 22 electrodes 142, some of these electrodes might produce non auditory percepts (e.g. facial stimulation or pain) and so would not be included in map data 222. Electrodes used in a map are referred to as "selected" or "activated" channels. It should also be appreciated that although there is a one-to-one correspondence between electrode 142 and channels, in alternative embodiments there is no such correspondence. Accordingly, map data 222 may also include data allocating each frequency band to, for example, an electrode pair.

Even though the device will normally be tested and re-adjusted after a period of time has elapsed, for example six-months from implantation or initial activation, an initial operational settings profile comprising the current level settings is initially generated. After the period of time has elapsed, the initial operational settings profile is optimized by re-adjusting operational settings profile containing current levels for each of the many channels.

Unlike conventional techniques for fitting a cochlear implant to the recipient in which the operational setting values of the stimulation channels are individually tested and set, embodiments of the present invention enable an operator to fit the implant through a parametric fitting process. In a parametric fitting process under embodiments of the present invention, an operational settings profile for a speech processor may include settings for multiple discrete current levels (CL), which are manipulated in embodiments of the present invention, not as individual or discrete settings, but rather collectively manipulated as a group. Profile adjustment functions, as will be further described below in conjunction with exemplary functions such as shift, tilt, curvature, and combinations thereof, are programmed in advance and are provided with function parameters from operators of the fitting system and apply the calculations and other tasks associated with each function to the operational settings profile. The function parameters are values such as +10 or −10 (for the shift function), +5 degrees or −5 degrees (for the tilt function), and so forth. Using function parameters with the profile adjustment function, the operational settings profile is manipulated or adjusted according to the selected adjustment function and the associated parameters received. As one of ordinary skill in the art will appreciate, profile adjustment functions as defined herein may also be referred to as "parameters,", for purposes of clarity only the term "profile adjustment functions" for which function parameters are received from the operator of the fitting system. In a parametric fitting system, profile adjustment functions may include vertical position shift, profile tilt and profile curvature, which are described in U.S. patent application Ser. No. 10/518,812, and may be applied simultaneously to the entire profile of T- and/or C-levels, in addition to other modifications made by a particular profile adjustment function. Such a global change to the entire profile provides numerous benefits including quicker and simpler changes of the T- and/or C-levels compared to manually testing and adjusting individual channels in the implanted device.

In certain embodiments of the present invention, parametric fitting methods and systems are provided which allow for parametric fitting of implants using profile adjustment functions that produce results which may be recognizable by the recipient as components of sound, namely bass and treble. By adjusting the recipient's operational settings profile using profile adjustment functions that produce recognizable components of sound, the recipient is better able to respond and provide meaningful responses to test signals sent from the fitting system. Although adjustments and manipulations are described below with respect to operational settings profiles for threshold settings ("T-levels"), it should be understood that the same or similar manipulations may be made with regard to operational settings profiles for C settings as well as operational settings profiles having combined T- and C-settings.

Where T-levels are being tested or adjusted, the stimuli used during this process are necessarily at the threshold of hearing or perception for the recipient. Therefore, the recipient may not be able to provide consistent or accurate responses when presented with the test stimulus. For example, it may be difficult for the recipient to distinguish between one volume of a test stimulus from the same stimulus having elevated volume or changed treble. Therefore, in an embodiment of the present invention, C-levels may first be determined followed by an interpolation or derivation of those C-levels in order to generate appropriate T-levels.

As used herein, a "channel" is a pair of electrodes that provides a path for current to flow. One electrode is an active electrode and the other is a reference electrode. Pulses of current flow from the reference electrode to the active electrode and back again to stimulate nearby neurons. In one embodiment of the present invention there are 22 channels, although other embodiments of the present invention may have a different number of channels.

Prior to adjusting the operational settings profile, an initial operational settings profile must be created or generated. The initial operational settings profile can be created through objective measuring techniques such as recording the electrically evoked auditory brain stem response (EABR) in the cochlear implant recipient. Alternatively, it is possible to objectively create the initial operational settings profile through measurements taken of the electrically evoked compound action potential (ECAP). These and other techniques for objectively setting the initial operational settings profile are discussed further in U.S. patent application Ser. No. 10/518,812 and International Application Number PCT/AU03/0084, which are hereby incorporated by reference herein in their entirety. Once the initial operational settings profile (comprising T- and C-levels for a plurality of channels) is generated, it can be adjusted or set using an embodiment of the present invention.

The initial operational settings profile may be generated, derived, or generic. The operational settings profile may be generated through direct measurements, for example, of the ECAP thresholds for each of the electrodes. Alternatively, it may be derived, for example, as a result of statistical analysis of recipient mapping data for a number of subjects, or the result of a number of electrophysiological and/or psychophysics measurements in combination with statistical analysis, such as multiple regression. It may also be derived by measuring threshold levels for only a small number of electrode channels and then predicting or interpolating the other electrode channels for which measurements were not taken.

Alternatively, the initial operational settings profile may also be generic in that a standard operational settings profile or even a constant value for all channels may be used as the initial operational settings profile. The initial operational settings profile is normally established without the need for subjective feedback from the recipient and without performing multiple tests on each electrode channel.

In FIG. 3, a GUI with T- and C-levels for a recipient map generated by a clinician during a mapping session using one embodiment of the present invention is shown. As noted previously with regard to FIG. 2, these levels have been generated using a software package developed to assist the clinician by providing a graphical interface that is easy for the clinician to manipulate and visualize. In other embodiments of the present invention, the software package may be configured to allow the recipient or other non-clinician operator to use the software package. The horizontal sections 304 numbered 1-22 (along the top) indicate the channel number along the intracochlear array of the implant, and the vertical axis 305 represents current levels 306 for each electrode channel in the array. This software package is run on a computer that outputs signals set by the software package through an interface adapted to connect to the speech processor and allow transmission of signals from the computer to the processing control system of the speech processor which in turn outputs stimulation signals via the transcutaneous radio frequency (BY) link to the implanted receiver/stimulator unit of the system. The computer is equipped with hardware interfaces such as, for example, a mouse, keyboard, stylus, touch-screen and joystick, among other types of input interface devices.

As shown in this particular embodiment of the present invention, the upper vertical limit 308 for each channel is the maximum comfort level (C-level) which represents for that particular channel, the maximum amount of current which can be delivered to deliver a sensation to the recipient at a loudness level which is just tolerable to that recipient. The lower vertical limit 310 for each channel is the threshold level (T-level) which represents the amount of current which can be delivered by that channel to produce a sensation that is just audible to the recipient. In this particular example, the T- and C-levels for a number of channels 304A-104G are specifically shown, for example the T- and C-levels for electrode channel 11 are 128 Current Units and 168 Current Units, respectively, and in use all sounds detected are mapped between these two levels to produce the equivalent sound sensation to the recipient. In this particular embodiment of the present invention, electrodes having higher numbers correspond to lower frequency channels and vice versa. So in FIG. 3, electrode 22 corresponds to the lowest frequency stimulation produced by the implanted hearing prosthesis, while electrode 1 corresponds to the highest frequency stimulation produced by the implanted hearing prosthesis.

In one embodiment of the present invention, the software package shown in FIG. 3 is programmed and configured so that the T- and C-levels, among other aspects of the operational settings profile, can be adjusted using the software package. As noted previously with regard to FIG. 2, the software package is configured to execute pre-programmed routines or functions that allow the software package to manipulate the operational settings profile in various ways. For example, in one embodiment, the software package includes program code for applying different adjustment functions, such as vertical position shift, profile tilt and profile curvature, bass control, and treble control, to values of an operational settings profile. Each of these functions are related to the definition of the "current level" scale, and may involve one or more sets of calculations which modify the values in the operational settings profile. It should be appreciated that a parallel shift is parallel in terms of current units, not, for example, in terms of microamps. In the GUI shown in FIG. 3, the operator 204 has selected to provider parameter values for the shift function. Operator 204 is able to provide parameter values for the T- and C-levels using input buttons 312A and 312B. When parameter values are provided in this manner, with this particular shift function, the entire C-level operational settings profile 306B is adjusted and/or the entire T-level operational settings profile 306A is adjusted accordingly.

Figure 4:
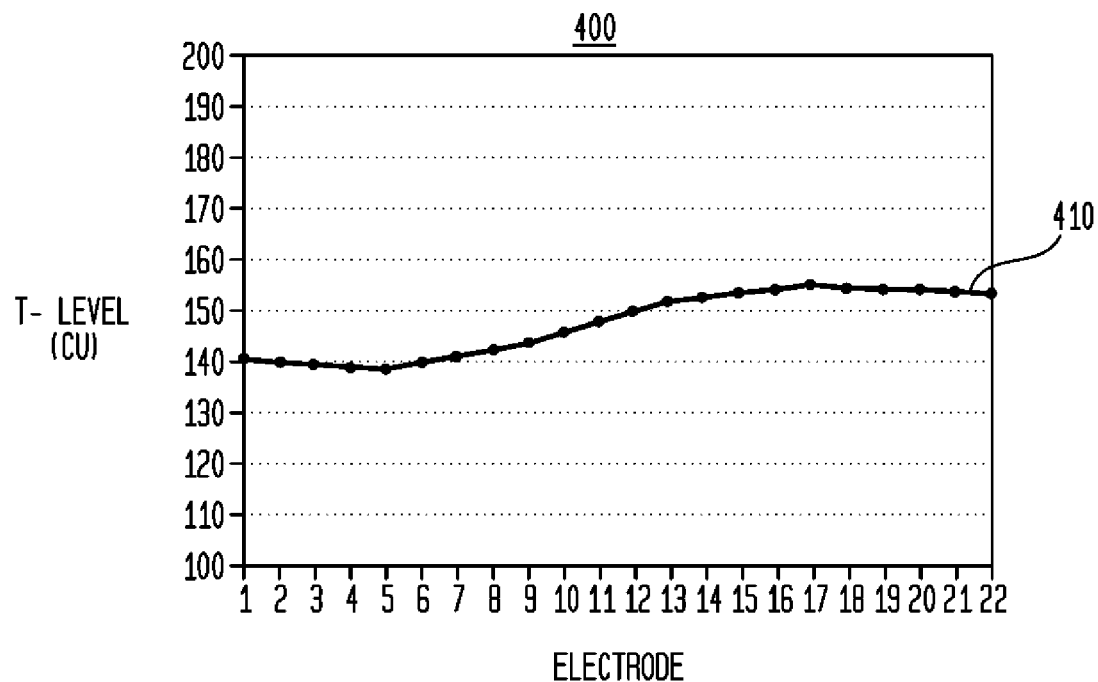
FIG. 4 is a graph of a current level (CL) profile for threshold (T) levels.
Figure 5:
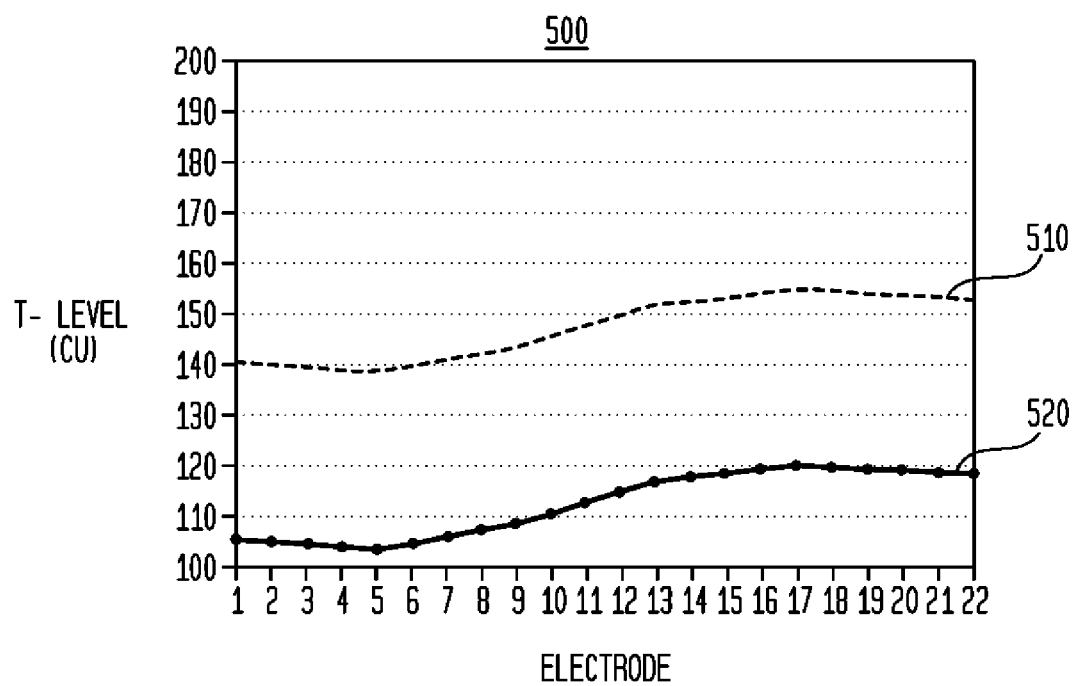
FIG. 5 is a graphical depiction of the speech processor ("SP") settings profile of FIG. 4 after having a shift profile adjustment function with a parameter of 25 CU applied to the operational settings profile according to an embodiment of the present invention.

According to one embodiment of the present invention, as illustrated in FIGS. 4 and 5, a vertical position shift function is applied to operational settings profile 410 (shown as 510 in FIG. 5) to produce operational settings profile 520. Function parameter values are received by the software package which uses the received value as an increment, to shift the operational settings profile by that increment. For example, for the operational settings profile 410 depicted in FIG. 4, a "−25" increment value is received for the vertical position shift function. Each time the operational settings profile is shifted, the software package reduces each of the T-levels of the operational settings profile by an increment of 25, thus moving the operational settings profile depicted in FIG. 4 down and resulting in the operational settings profile depicted in FIG. 5.

Other functions may be applied to the operational settings profile which does not make identical adjustments to each level of the operational settings profile, as in the case of applying a shift function, as described above. For example, in one embodiment of the present invention, a tilt function may be programmed such that a constantly varying percentage of a parameter value is applied to the operational settings profile. For example, for the operational settings profile depicted in FIG. 4, if a "+10" tilt parameter value is provided to the software package, the software package may apply a constantly varying percentage of +10 to the operational settings profile depicted, to result in the operational settings profile as depicted in FIG. 4. As can be seen in FIG. 4, the T-level for electrode 22 increased by 10 CU, while the T-level for electrode 1 decreased by 10 CU. For the channels in between, a constantly variable percentage of 10 CU was applied. For example, for electrode 21, 90% of 10 CU may be applied; for electrode 20, 85% of 10 CU may be applied; for electrode 19, 80% of 10 CU may be applied, and so forth.

In this embodiment of the present invention, a fulcrum or rotation point was designated as electrode 12. However, it is to be understood that in other embodiments of the present invention, the rotation point may be set at one end of the series of channels or the other, or some point in between the two extremities other than electrode 12. Furthermore, it is to be understood that the rotation point may be manually designated by the clinician, the recipient, or other operator of the software package, rather than being pre-set, for example, as electrode 12.

Similarly, to modify the profile curvature, various calculations may be performed on the operational settings profile based on parameter values received from the operator of the software package. For example, using formulas from coordinate geometry based on two or more selected operational settings profile T-levels, the profile curvature may be manipulated to increase the rate of curvature of the waveform defined by the T-levels in the operational settings profile. Oppositely, based on two or more operational settings profile T-levels selected, the profile curvature may be decreased using the parameter values received and various calculations used to calculate the curvature. In certain embodiments of the present invention, a fulcrum or rotation point, for example electrode 12, may be pre-set. In other embodiments of the present invention, the operator is able to provide a rotation point and other information which may be used in applying the curvature function to the operational settings profile. The rotation point need not be along the waveform being manipulated In addition to the aforementioned profile adjustment functions, bass control and treble control parameters may be implemented using a combination of the calculations underlying the tilt and curvature parameters or by using both the tilt and curvature functions together. Although the tilt and curvature parameters may be utilized with the shift parameter in a parametric fitting process of the implant, adjustments using the tilt and curvature parameters are not easily recognizable by recipients as the adjustments do not produce effects which are within the generally accepted vocabulary of describing sound. In other words, the adjustments using tilt and curvature parameters are not always clearly related to aspects of sound that are readily identifiable to an implant recipient. Thus it is desirable to use other functions in addition to or instead of tilt and curvature parameters which are more easily recognizable when interactively adjusting aspects of an operational settings profile with an implant recipient.

According to the present invention, tilt and curvature functions may be combined and presented to the recipient as bass and treble functions, which the recipient may recognize as components or aspects of sound. Responding to bass and treble functions, the recipient will be able to provide more meaningful responses during the fitting process. Bass and treble functions are produced by altering the current values of the operational settings profile by providing more or less low-frequency stimulation, hence affecting the bass, or by providing more or less high-frequency stimulation, hence affecting the treble.

Figure 6:
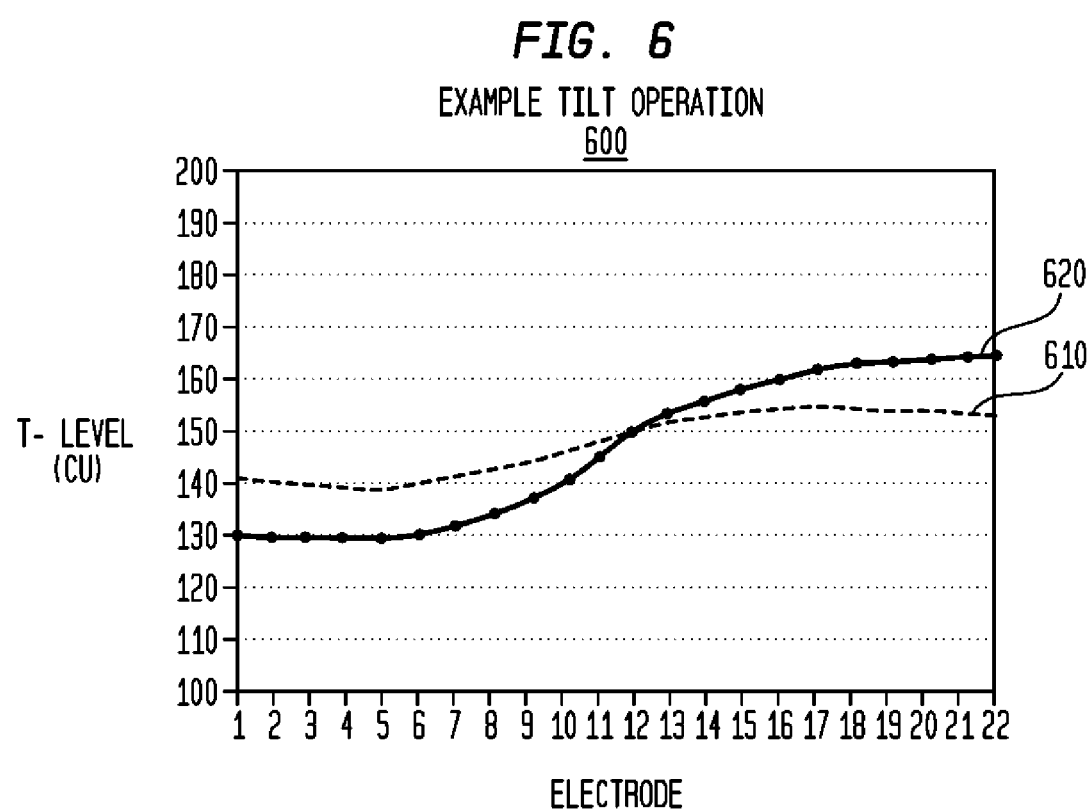
FIG. 6 is a graphical depiction of the operational settings profile of FIG. 4 after having a tilt profile adjustment function with a parameter of +10 CU applied to the operational settings profile according to an embodiment of the present invention.

In certain embodiments of the present invention, bass control and treble control may be implemented by using just values received for tilt and curvature functions, rather than receiving values for direct use in applying bass control or treble control function parameters. In one particular embodiment of the present invention, tilt and curvature values are used to apply bass control or treble function parameters or otherwise used to achieve bass control or treble control. For example, for the operational settings profile of T-levels depicted in FIG. 4, a bass profile adjustment function is produced using the operational settings profile by combining a tilt profile adjustment function with a function parameter value of +10 (producing an operational settings profile 620 as depicted in FIG. 6) and a curvature profile adjustment function with a function parameter value of +3 (producing an operational settings profile 720 of T-levels as depicted in FIG. 7.) In this particular example, the curvature was applied such that the values of the operational settings profile from electrode 12 down to electrode 1 remained largely unchanged, while the values of electrode 13 up to electrode 22 were modified by applying the curvature profile adjustment function. The net effect of applying this bass function by applying the combination of tilt and curvature functions is that the resulting profile produces an altered amount of stimulation in the lower frequency channels (e.g., those electrodes closer to electrode 1) while it produces the same amount of stimulation in the higher frequency channels (e.g., at those electrodes closer to electrode 22) thus producing bass control. A similar process for combining tilt and curvature function adjustments to produce treble control may be used to impact those channels in the higher frequencies while maintaining those channels in the lower frequencies largely unchanged.

In another embodiment of the present invention, rather than receiving function parameters for tilt and curvature and then producing bass or treble effects, the software package may be configured to receive and directly bass and treble function parameters to directly modify the waveform. In this embodiment of the present invention, a look-up-table or pre-programmed formulas may be applied to enable a conversion of the bass or treble parameter value into necessary tilt and/or curvature values for use in implementing the requested adjustment.

In a further embodiment of the present invention, when applying bass or treble parameters, instead of applying a combination of tilt and curvature functions, a selected portion of the established operational settings profile is modified, rather than having a global modification of all operational settings profile levels. In one embodiment of the present invention, the levels of the profile 410 depicted in FIG. 4 which correspond to electrodes 1 to 12 are made subject to a tilt function, or otherwise modified, to produce the operational settings profile 720 as depicted in FIG. 7. The operational settings profile, as depicted in FIG. 7, produced using this embodiment of the present invention is practically identical to the operational settings profile produced using the combination of the tilt and curvature profiles, as described above.

Figure 8A:
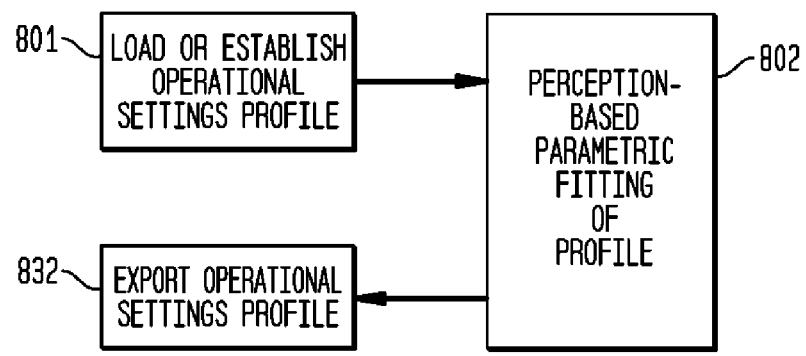
Figure 8B:
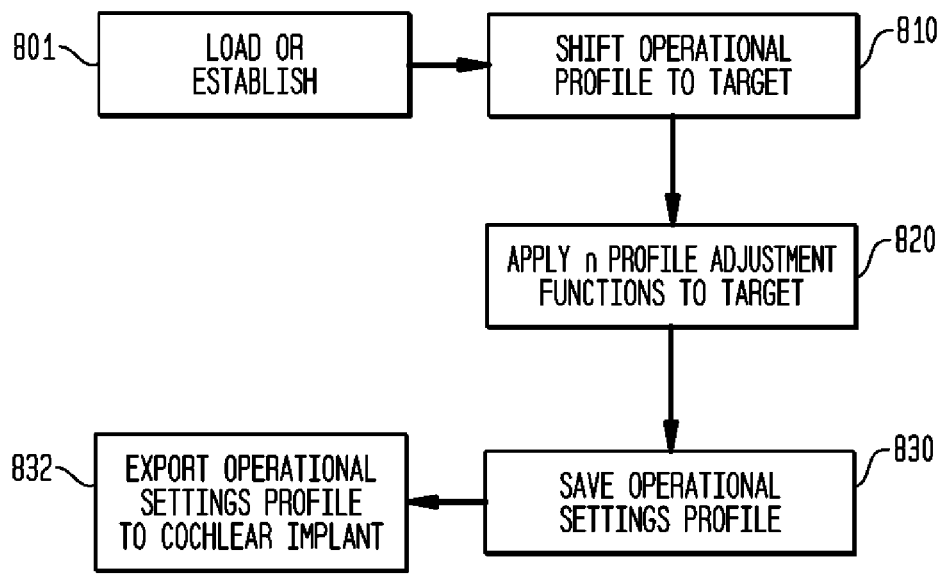

The overall process of adjusting the T- and C-levels after the implant is placed is illustrated in the flowchart depicted in FIGS. 8A-8C according to one embodiment of the present invention. As depicted in FIG. 8A, in one embodiment of the present invention, the operational settings profile for the recipient is established, loaded, or imported into fitting arrangement 200. Perception-based parametric fitting is performed as described herein in block 802 and the resulting operational settings profile is exported into either or both of the recipient's speech processor or other storage location.

As shown in FIG. 8B, perception-based parametric fitting 802, according to one embodiment of the present invention, comprises shifting 810 the operational settings profile to a desired target level, based on the recipient responses to test signal 212. Following shifting 810, one or more function parameters ("n parameters") are applied 820 to the operational settings profile. Afterwards, the shifted and adjusted operational settings profile is saved 830 prior to being exported 832 from the fitting arrangement 200.

As described above, in one embodiment of the present invention, am operational settings profile to be tested and/or adjusted is either loaded from, or established 801 at, the speech process or other component of the hearing prosthesis into the computer executing the software package. All T- or C-levels of the operational settings profile are initially moved down 803 so that they do not exceed the threshold or maximum comfort level before testing has even started. In the case of setting the T-level profile, the initial operational settings profile would be shifted down to a level that would be below a recipient's threshold of hearing; for example, the maximum current level of the operational settings profile could be reduced to a current level of 80 with all other levels being relative to this. In the case of setting the C-level profile, the initial CL, profile could be moved to any level that is below the maximum comfort level of the recipient as a starting point, for example, the previously identified threshold.

The recipient is presented 812 with a broad band signal, for example a live speech sample, and the stimulation representative of this signal is delivered by the electrode array of the implant to the recipient within the constraints of the operational settings profile. It is to be understood that the broad band signal may comprise other types of signals, including but not limited to artificially generated sounds or recorded signals. A response is received 814 from the recipient as to whether the test stimulus was detected or heard by the recipient (when adjusting the T-level operational settings profile) or when the recipient is no longer comfortable with the volume level of the test stimulus (when adjusting the C-level operational settings profile). If the recipient does not detect the live speech (in the case of setting the T-level operational settings profile), the operational settings profile is then shifted up or increased 815 by a single step or increment 815 (for example iterations of current levels at a time). This process of presenting, receiving a response from the recipient, and shifting the CL-profile up by an increment is repeated until the target is reached 814. When setting the T-level operational settings profile, the target is the point at which the recipient initially detects the test stimulus. When setting the C-level operational settings profile, the target is the point at which the maximum comfort level is reached.

After repeating the above process until the relevant target is reached, the last version of the operational settings profile is shifted down by one increment. Then the profile is further manipulated 820 by applying other function parameters from a predefined set of functions, to further change the characteristics of the operational settings profile. In one embodiment of the present invention, a "tilt" function is applied to the profile, by adding/subtracting a calculated amount to/from each individual current level value for each channel of the electrode array. This manipulation literally causes a "tilt" of the profile by rotating the waveform up for the high frequency channels and down for the low frequency channels as depicted in FIG. 4, or vice versa.

The operational settings profile is manipulated by using the "tilt" value, until the live speech is no longer detected, i.e. the target is not met 826. Then, the shift function as described above is repeated until the recipient can again detect the live speech.

If no further shift/tilt combination meets the target criteria (i.e. sound detection in this example), then the current value for shift is the target shift value. This operational settings profile is then saved 830 and exported to the hearing prosthesis 832.

Whilst this process has been shown only in relation to setting the T-levels, it can easily be used to set the C-levels, with the only change required being the criterion of the "target." For setting the C-levels, the "target" criterion is maximum comfort of sound perceived by the recipient, rather than sound detection, as is the case in setting the T-levels.

Further, whilst the process described above has combined the shift and tilt functions, the two functions can be applied separately. In this regard, the shift function can be used to move the operational settings profile to a threshold or maximum comfort position where the tilt or other such functions can be applied to the operational settings profile to optimize and fine tune the operational settings profile.

Furthermore, in other embodiments of the present invention, the procedure described for producing bass and treble controls can be optimized by a multivariate statistical technique such as rotation of the two tilt and curvature components. In this regard, the biquartimax procedure yields particularly good results. Since these functions are clearly related to certain aspects of sound and can be readily perceived by an implant recipient, they enhance the interactive fitting of an implant. In the method of the present invention the manipulation of the operational settings profile can therefore be performed by manipulating the bass and treble characteristics of the profile.

Using one embodiment of the present invention, an actual fitting process as described above was accomplished in less than 5 minutes. The recipient reported that sound perception using the map created by the present invention was substantially the same as the sound perception using the map created by the conventional mapping techniques which take a substantially greater amount of time.

The present invention therefore requires minimal psychophysics measurements using live voice, compared to many psychophysical measurements (roughly equivalent to twice the number of channels) using artificial stimuli as is the case in conventional mapping procedures. As a result, the present invention provides a programming/mapping procedure that is more recipient friendly, and makes the fitting procedure, especially for small children, simpler, more time efficient and more cost effective then has historically been the case. Furthermore, by allowing for a fitting process which presents changes using recognizable aspects of sound to the recipient, such as bass and treble, the recipient is able to better interact with the clinician or system during fitting. With better subjective comprehension and interaction during fittings, the recipient is even able to conduct the fittings themselves, even without the aid of a clinician or at remote locations outside the presence of a clinician.

Further features and advantages of the present invention are described in application Ser. No. 10/518,812, filed Oct. 11, 2005, which is a National Phase Application of International Application No. PCT/AU03/0084, filed on Jun. 26, 2003, which claims priority from Australian Patent Application No. PS 3182, filed Jun. 26, 2002, which are hereby incorporated by reference herein.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A method of adjusting an established initial operational settings profile, the operational settings profile having two or more operational setting values for a speech processor of a recipient's cochlear implant, comprising:
    setting one or more profile adjustment functions with one or more function parameters, wherein said one or more profile adjustment functions comprise a tilt function; and
    modifying concurrently said two or more operational setting values in said operational settings profile using set one or more profile adjustment functions, wherein said two or more operational setting values comprise threshold (T) and comfort (C) levels.

2. The method of adjusting according to claim 1, wherein the one or more profile adjustment functions comprise a shift function configured to either increase or decrease said two or more operational setting values in said operational settings profile by a fixed amount.

3. The method of adjusting according to claim 2, wherein modifying concurrently said two or more operational setting values comprises modifying only a subset of said values in said operational settings profile to produce bass and/or treble effects.

4. The method of adjusting according to claim 2, wherein the one or more profile adjustment functions further comprise a curvature function.

5. The method of adjusting according to claim 4, further comprising:
    applying a combination of the tilt and curvature profile adjustment functions to modify the operational setting values of the operational settings profile to produce bass and treble effects with the cochlear implant for the recipient.

6. The method of adjusting according to claim 1, further comprising:
    creating a waveform based on said two or more operational setting values; and
    selecting a rotation point along said waveform about which said waveform may be rotated during said modifying said two or more operational setting values.

7. The method of adjusting according to claim 5, wherein said modifying concurrently said two or more operational setting values is performed in the presence of a broadband signal.

8. The method of adjusting according to claim 5, wherein said tilt and curvature functions comprise adding/subtracting a derived amount of current level from said two or more operational setting values in said operational settings profile.

9. A programmable apparatus configured to adjust an established initial operational settings profile, the operational settings profile having two or more operational setting values for a speech processor of a recipient's cochlear implant, comprising:
    a processor configured to execute computer code;
    a software package executed by said processor and configured to receive one or more operator inputs;
    an interface configured to communicatively couple said processor with an auditory stimulation system and further configured to retrieve and store the operational settings profile,
    wherein said software package is configured to set one or more profile adjustment functions with one or more function parameters, and further configured to modify concurrently said two or more operational setting values in said operational settings profile using set one or more profile adjustment functions, wherein said two or more operational setting values comprise threshold (T) and comfort (C) levels, wherein said one or more profile adjustment functions comprise a tilt function.

10. The apparatus of claim 9, wherein the one or more profile adjustment functions comprise a shift function configured to either increase or decrease said two or more operational setting values in said operational settings profile by a fixed amount.

11. The apparatus of claim 9, wherein the one or more profile adjustment functions further comprises bass and treble functions.

12. The apparatus of claim 9, wherein the one or more profile adjustment functions further comprise a curvature function.

13. The apparatus of claim 12, wherein said software package is further configured to apply a combination of the tilt and curvature profile adjustment functions to concurrently modify the two or more operational setting values in said operational settings profile to produce bass and treble effects with said cochlear implant for the recipient.

14. The apparatus of claim 13, wherein said software package is further configured to add/subtract a derived amount of current level from said two or more operational setting values in said operational settings profile.

15. The apparatus of claim 9, wherein said software package is further configured to create a waveform based on said two or more operational setting values, and to select a rotation point along said waveform about which said waveform may be rotated during said modification of said two or more operational setting values.

16. A programmable apparatus configured to adjust an established initial operational settings profile, the operational settings profile having two or more operational setting values for a speech processor of a recipient's cochlear implant, comprising:
    means for setting one or more profile adjustment functions with one or more function parameters, wherein said one or more profile adjustment functions comprise a tilt function; and
    means for modifying concurrently said two or more operational setting values in said operational settings profile, wherein said two or more operational setting values comprise threshold (T) and comfort (C) levels.

17. The apparatus according to claim 16, further comprising means for modifying only a subset of said two or more operational setting values in said operational settings profile to produce bass and/or treble effects.

18. The apparatus according to claim 16, wherein the one or more profile adjustment functions further comprise a curvature function.

19. The apparatus according to claim 18, further comprising:
    means for applying a combination of the tilt and curvature profile adjustment functions to modify said two or more operational setting values in said operational settings profile to produce bass and treble effects.

20. The apparatus according to claim 16, further comprising:
    means for creating a waveform based on said two or more operational setting values; and
    means for selecting a rotation point along said waveform about which said waveform may be rotated.

21. The method of adjusting according to claim 1, wherein the one or more profile adjustment functions further comprise a curvature function.

* * * * *